United States Patent [19]

Hilmersson

[11] Patent Number: 5,569,438
[45] Date of Patent: Oct. 29, 1996

[54] APPARATUS FOR STERILIZING A CONTINUOUS PACKAGING MATERIAL WEB

[75] Inventor: Anders Hilmersson, Lund, Sweden

[73] Assignee: Tetra Laval Holdings & Finance S.A., Pully, Switzerland

[21] Appl. No.: 390,503

[22] Filed: Feb. 17, 1995

Related U.S. Application Data

[62] Division of Ser. No. 115,787, Sep. 3, 1993, Pat. No. 5,424,034, which is a continuation of Ser. No. 913,054, Jul. 14, 1992, abandoned.

[30] Foreign Application Priority Data

Jul. 17, 1991 [SE] Sweden .................................. 9102190

[51] Int. Cl.⁶ .............................. A61L 2/06; A61L 2/20; B65B 55/06; F26B 3/04
[52] U.S. Cl. .............................. 422/293; 34/339; 34/350; 34/389; 34/414; 34/415; 34/426; 34/459; 34/503; 53/425; 422/292; 422/300; 422/306
[58] Field of Search .................................. 422/28, 31, 33, 422/292, 293, 300, 306, 405; 34/330, 337, 339, 343, 348, 350, 389, 44, 415, 426, 444, 446, 459, 503; 53/425, 426

[56] References Cited

U.S. PATENT DOCUMENTS

| | | |
|---|---|---|
| 3,577,653 | 5/1971 | McClenathan et al. . |
| 3,854,874 | 12/1974 | Loliger et al. . |
| 3,904,361 | 9/1975 | Egger . |
| 3,933,428 | 1/1976 | Egger . |
| 3,947,249 | 3/1976 | Egger . |
| 4,055,035 | 10/1977 | Sjöstrand et al. ........................ 53/167 |
| 4,255,556 | 9/1980 | Löthman et al. .......................... 422/28 |
| 4,888,155 | 12/1989 | Posey et al. ................................. 422/49 |
| 5,022,167 | 6/1991 | Nakamura .................................. 34/160 |
| 5,114,670 | 5/1992 | Duffey ....................................... 422/24 |
| 5,114,671 | 5/1992 | Olanders .................................... 422/28 |
| 5,424,034 | 6/1995 | Hilmersson ................................. 422/28 |

FOREIGN PATENT DOCUMENTS

| | | |
|---|---|---|
| 0361858 | 9/1988 | European Pat. Off. . |
| 461264 | 5/1988 | Sweden . |

Primary Examiner—Robert J. Warden
Assistant Examiner—Krisanne M. Thornton
Attorney, Agent, or Firm—Burns, Doane, Swecker & Mathis

[57] ABSTRACT

In an apparatus for treating, for purposes of sterilization, a continuous material web a first treatment station is provided and includes a device for bringing a material web into contact with liquefied hydrogen peroxide. A second treatment station is also provided in which the material web is simultaneously sterilized with hydrogen peroxide vapor and dried with heated air after treatment of the material web in the first treatment station. The second treatment station includes an elongate chamber having an inlet and outlet, the material web being dried and thereby generating hydrogen peroxide vapor as it is led through the elongate chamber from the inlet to the outlet. The second treatment station also includes an outer flow duct in flow communication with the inlet and outlet of the elongate chamber. Heated, hydrogen peroxide-free air is supplied into the outer flow duct such that a portion of the hydrogen peroxide vapor generated by drying the material web and the heated air flows from the elongate chamber into the outer flow duct and mixes with supplied air to form a mixture, and such that the mixture flows through the elongate chamber in the direction of movement of the material web.

13 Claims, 2 Drawing Sheets

APPARATUS FOR STERILIZING A CONTINUOUS PACKAGING MATERIAL WEB

This application is a divisional of application Ser. No. 08/115,787, now U.S. Pat. No. 5,424,034 filed Sep. 3, 1993, which is a continuation of application Ser. No. 07/913,054 filed Jul. 14, 1992, now abandoned.

TECHNICAL FIELD

The present invention relates to a method of treating, for sterilization purposes, a continuously running material web, according to which method the whole of the web or parts thereof intended for sterilization are brought into contact with liquefied hydrogen peroxide and thereafter dried with the aid of a hot gaseous fluid.

The present invention also relates to an apparatus for treating, for sterilization purposes, a continuously running material web, the apparatus comprising a first treatment station including a device for bringing all of the web or parts thereof intended for sterilization into contact with liquefied hydrogen peroxide, and a second treatment station including a device for drying the material web with the aid of hot gaseous fluid.

BACKGROUND ART

In packaging technology, use is often made of so-called aseptic packaging techniques in order to impart longer shelf-life to and facilitate the distribution of foods and pharmaceuticals and other types of products which are particularly perishable and/or sensitive to bacterial attack. Fundamentally, the principle of the aseptic packaging technique is based on filling and sealing the product in packages which are ready for distribution, under sterile or bacteria-free conditions, in order to create the best possible circumstances for transporting and storing the product in the unopened package with retained freshness qualities during lengthy periods of time from the date of packaging and without any need for cold storage. In order that such a sterile or aseptic package be technically feasible, it is necessary that both the product which is to be packed and the material from which the package is produced are sterilized, and that the filling of the sterilized product into the package made from the sterilized packaging material be carried out under such conditions that the risk of reinfection of the product is eliminated entirely or to all intents and purposes.

A very large group of known aseptic packages for products of the type mentioned above are now most generally produced with the aid of modern, rational packaging machines of the type which, either from a web or from prefabricated blanks of a packaging material, both form, fill and seal the finished cartons or packages. Packages are produced from, for instance, a single web in that the web is first sterilized by being brought—entirely or in parts intended for sterilization—into contact with liquefied hydrogen peroxide in that the web is led down into and through a heated hydrogen peroxide bath. After passage through the hydrogen peroxide bath, the web is passed through the nip between two cooperating and co-rotating nip rollers or cylinders with whose aid any entrained surplus of hydrogen peroxide will be removed from the web and recycled to the hydrogen peroxide bath. Thereafter, the web is dried with the aid of a hot gaseous fluid, for example sterile air, which is blown towards one or both faces of the web in order to dispel any residual hydrogen peroxide. After the drying operation, the web is reformed into a tube by both longitudinal edges of the web being united with one another in a longitudinal overlap seam or joint. The tube is filled with the relevant product (previously heat-treated or otherwise sterilized) and is divided into closed, combined package units by repeated transverse sealings of the tube below the product level in the tube. The package units are separated from one another by transverse incisions in the transverse sealing zones and are given the desired geometric—normally parallelepipedic—final form by a final forming and sealing operation during which the double-walled triangular corner flaps of the cushion-shaped package units are folded in and sealed against the outside of adjacent package walls. In order to avoid reinfection of the sterilized product, both the sterilization of the packaging material and the package forming and filling operations are carried out in an environment screened-off from the unsterile surroundings of the package by hot sterile air operating at slight excess pressure in relation to the ambient pressure.

In the above-described manner, aseptic packages are produced which possess good mechanical strength and configurational stability and further display superior chemical and bacterial tightness properties which create every potential for readily being able to handle and store the product in an unbroken package, with retained or but insignificantly affected freshness qualities during lengthy periods of time from the date of packing.

SUMMARY OF THE INVENTION

However, according to the present invention, it has surprisingly proved that it is feasible to realize aseptic packages with further improved sterility properties and consequentially improved preconditions for being able to package and store products which are perishable and sensitive to bacterial attack, with retained or but insignificantly affected freshness qualities under guaranteed extended storage times after the packing date. One object of the present invention is, therefore, to suggest guidelines as to how such improved aseptic packages may simply be produced with the aid of existing or slightly modified or retrofitted conventional equipment.

The object according to the present invention will be attained in that a method of the type described by way of introduction has been given the characterizing feature that the gaseous fluid consists of hydrogen peroxide-containing air, i.e. air which has been intentionally supplied with hydrogen peroxide.

The present invention springs in essence from the per se known fact that bacteria die in a hot, hydrogen peroxide filled atmosphere, and practical experiments which have been conducted show that the extermination of bacteria (log red) can be increased by at least 1.5 to 2 units (BsA) by drying the web or those parts of the web intended for sterilization with hot hydrogen peroxide-containing air, instead of employing solely hot air as previously.

A further object of the present invention is to propose a simple apparatus with whose aid the method according to the present invention may readily be reduced into practice.

This object is attained by means of an apparatus of the type described below.

BRIEF DESCRIPTION OF THE DRAWING FIGURES

The present invention will now be described and explained in greater detail hereinbelow, with particular reference to the accompanying drawing figures.

FIG. 1 is a schematic view of an apparatus in accordance with the present invention; and, FIG. 2 is a schematic view of the apparatus of FIG. 1 in which a liquid hydrogen peroxide bath is used to wet a material web.

DETAILED DESCRIPTION OF PREFERRED EMBODIMENTS

Figure 1:
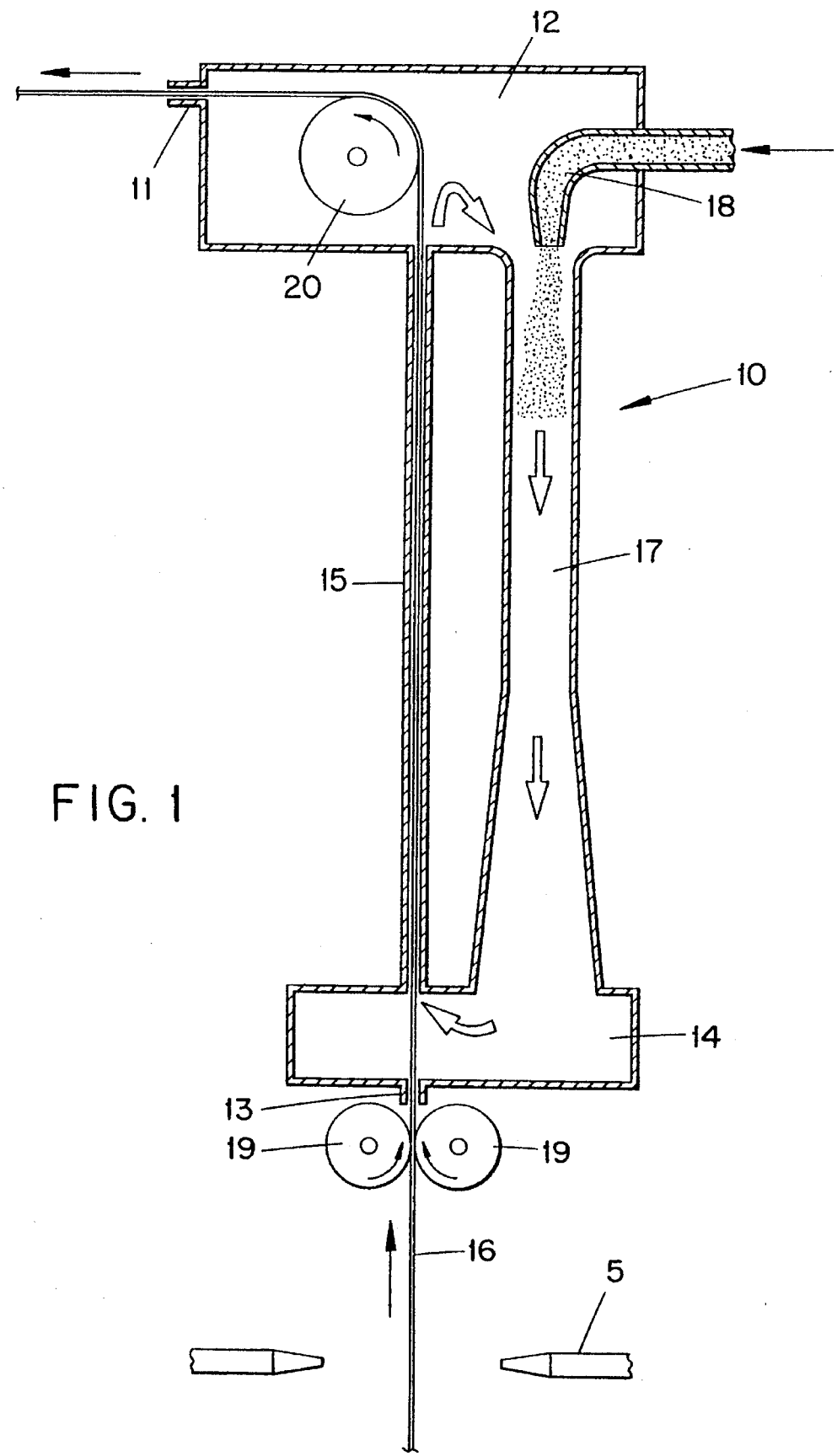

Referring to the drawing figures, the apparatus has been given the generic reference numeral 10. The apparatus 10 includes an outlet chamber 12 fitted with an outlet 11 and disposed at the upper region of the apparatus, and an inlet chamber 14 disposed at the lower region of the apparatus and fitted with an inlet 13. Both of the chambers 12 and 14 are in fluid communication with one another through an elongate space 15 extending substantially vertically between the chambers and through which a material web 16 is disposed to be led for contact with hydrogen peroxide-containing air which is simultaneously caused to flow through the elongate space 15 in the direction of movement of the material web for drying the web. The two chambers 12 and 14 are further interconnected with one another by the intermediary of an outer flow duct 17 extending between them for recycling at least a portion of the hydrogen peroxide-containing air flowing through the elongate space 15 from the outlet chamber 12 to the inlet chamber 14 for admixture of hot hydrogen peroxide-free air which is arranged to be supplied through an injector 18 discharging in the outlet chamber 12.

Ahead of the inlet 13 for the material web in the inlet chamber 14, there are disposed two co-rotating nip rollers of nip cylinders 19 between which the material web 16 is disposed to be led for mechanical dispelling of liquefied hydrogen peroxide which has accompanied the material web 16 and with which the web, or parts thereof intended for sterilization, has been brought into contact for the destruction of bacteria.

Figure 2:
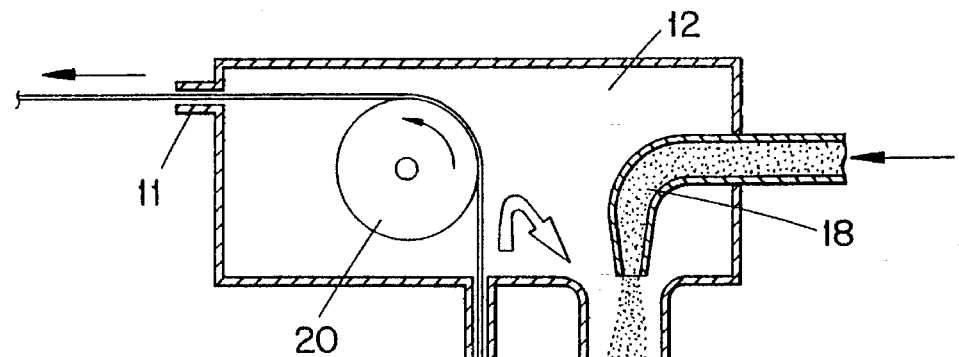
Figure 2:
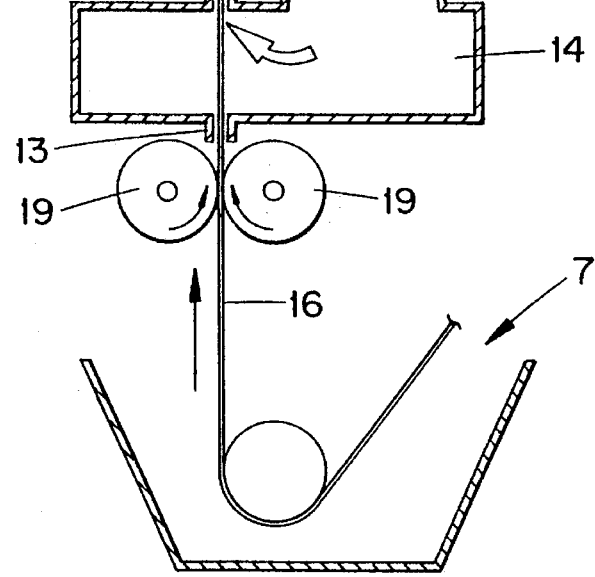

In a preceding treatment station, the liquefied hydrogen peroxide serving as sterilization agent for the web can have been applied to the web or those parts thereof intended for sterilization, either with the aid of spray nozzles 5 directed towards one or both faces of the web, as shown in FIG. 1, or similar spray devices with whose aid the liquefied hydrogen peroxide is applied in spray-mist or finely-divided form to the web for the formation of a hydrogen peroxide film covering all or the above-mentioned parts of the web. Alternatively, as illustrated in FIG. 2, the liquefied hydrogen peroxide may have been applied to the web by means of a heated hydrogen peroxide bath through which the web is led in the preceding treatment station.

At the upper region of the apparatus, there is disposed, in the outlet chamber 12, a co-rotating bending roller or conducting roller 20 about which the material web 16 is disposed to be led for deflection of the direction of movement of the material web such that the material web may pass freely throughout the entire apparatus from the inlet 13 to and out through the outlet 11 disposed at a right angle to the inlet 13.

In order to ensure good contact between the material web 16 and the hydrogen peroxide-containing air flowing through the elongate space 15, the elongate space 15 is preferably in the form of a narrow elongate gap whose dimensions substantially correspond to, or slightly exceed, corresponding dimensions of the passing material web. Similarly the outlet 11 and the inlet 13 are designed as narrow gap apertures dimensioned in accordance with the geometric dimensions of the material web and contributing to sealing off the apparatus from its outer, unsterile surroundings.

The apparatus 10 may be integral in or constitute a part of a conventional packaging machine of the type which, from the material web 16, both forms, fills and seals finished aseptic packages in the manner described in the foregoing, the apparatus 10 being placed in a so-called aseptic housing at the packaging machine, between the previously-mentioned station for applying liquefied hydrogen peroxide to the material web intended for sterilization and a tube-forming and product-filling station (not shown) of the packaging machine. While not being apparent from the drawing figures, it will be obvious to a person skilled in the art that the preceding hydrogen peroxide treatment station of the packaging machine and the subsequent tube-forming and product-filling station are, like the illustrated intermediate drying station well-protected from the outer, unsterile ambient atmosphere of the packaging machine and are preferably housed in a common machine casing (not shown) substantially completely sealed-off from the surroundings so as to prevent the penetration of bacteria and the consequential risk of reinfection of the sterilized and dried material web 16.

According to the present invention, the procedure is as follows for treating, for sterilization purposes, a continuously running material web with the aid of the above-described apparatus 10. The material web 16 which has been treated with hydrogen peroxide and mechanically scraped (or 'doctored') by means of the nip rollers 19 is led via the inlet 13 into the inlet chamber 14 of the apparatus into and through the elongate space 15 which, at the same time, is supplied with hot hydrogen peroxide-containing air from the outer flow duct 17 for contact with the web for dispelling remaining hydrogen peroxide residue. In this instance, the material web is displaced at a speed of approx. 0.4 m/sec., while the hydrogen peroxide-containing air (which has, at the inlet chamber 14, a temperature of approx. 150° C. and a hydrogen peroxide concentration of approx. 10,000 ppm) flows through the elongate space 15 in the direction of movement of the material web at a speed of approx. 20 m/sec. From the elongate space 15, the dried material web 16 is led via the bending roller or conducting roller 20 into the outlet chamber 12 of the apparatus out through the outlet 11 together with a minor accompanying flow of hydrogen peroxide-enriched air (approx. 0.01 kg/sec.), while a major fraction of the hydrogen peroxide-enriched air (approx. 0.04 kg/sec.) after passage through the space 15 is recycled to the inlet chamber 14 via the outer flow duct 17 for new contact with the material web 16. In the outer flow duct 17, the thus recycled hydrogen peroxide-enriched air, which, after the drying of the material web in the elongate space 15, is at a temperature of approx. 80° C. in the outlet chamber 12, is mixed with hot (approx. 400° C.) hydrogen peroxide-free air which is continuously fed to the injector 18 discharging in the outlet chamber 12 at a speed of approx. 100 m/sec in a quantity corresponding to that air volume which accompanies the material web 16 out through the outlet 11, i.e. approx. 0.01 kg/sec, so as to adjust the hydrogen peroxide content and temperature of the recycled hydrogen peroxide-containing air flow at approx. 10,000 ppm and 150° C., respectively, at the inlet chamber 14 and prior to entry into the elongate space 15 for new drying of the material web 16.

In the manner described above, it has proved to be possible to increase the destruction of bacteria on the material web 16 by at least 1.5–2 units (log red in respect of BsA) and thereby correspondingly improve the preconditions for producing aseptic packages from the material web treated using the method according to the present invention, as compared with conventional techniques according to which the material web is dried using hot hydrogen peroxide-free or hydrogen peroxide-poor air.

It might finally be pointed out that the method according to the present invention, while having been described in the context of packaging material webs such as webs of plastic-coated paper, is not, naturally, restricted exclusively to this practical application but could just as well be employed on other types of material webs which, for purposes of sterilization, are brought into contact with liquefied hydrogen peroxide and thereafter dried for dispelling remaining hydrogen peroxide residue from the web.

The present invention should not be considered as restricted to that described above and shown in the drawing figures, many modifications being conceivable without departing from the spirit and scope of the appended claims.

What we claim and desire to secure by Letters Patent is:

1. An apparatus for treating, for purposes of sterilization, a continuous material web comprising:
    a first treatment station including means for bringing a material web into contact with liquefied hydrogen peroxide; and
    a second treatment station including means for simultaneously sterilizing the material web with hydrogen peroxide vapor and drying the material web with heated air after treatment of the material web in the first treatment station, the second treatment station including an elongate chamber having an inlet and outlet, the material web being dried and thereby generating hydrogen peroxide vapor as it is led through the elongate chamber from the inlet to the outlet,
    an outer flow duct connecting the inlet and outlet of the elongate chamber for returning a circulating flow from the outlet to the inlet, and
    means for supplying heated, hydrogen peroxide-free air into the outer flow duct such that hydrogen peroxide vapor generated by drying the material web and the heated air flows from the elongate chamber into the outer flow duct and mixes with the supplied heated, hydrogen peroxide-free air to form a mixture, and such that the mixture flows through the elongate chamber in the direction of movement of the material web.

2. The apparatus as claimed in claim 1, wherein said means for supplying heated air without hydrogen peroxide include an injector discharging in the flow duct.

3. The apparatus as claimed in claim 1, wherein the inlet and outlet of the elongate chamber for the material web consist of apertures having dimensions that exceed the corresponding dimensions of the material web.

4. The apparatus as claimed in claim 1, wherein the inlet and outlet of the chamber are positioned in planes at right angles to one another and the chamber is provided at the outlet end with a roller disposed in the chamber to guide the material web during passage through the chamber and out the outlet.

5. The apparatus as claimed in claim 1, wherein the means for bringing the web into contact with liquefied hydrogen peroxide comprises a heated hydrogen peroxide bath in which the material web is submerged.

6. The apparatus as claimed in claim 5, further comprising two nip rollers disposed between the bath and the inlet of the elongate chamber between which the material web is led for removing surplus liquefied hydrogen peroxide prior to entering the elongate chamber.

7. The apparatus as claimed in claim 1, wherein the means for bringing the material web in contact with liquefied hydrogen peroxide comprises nozzles to spray atomized liquefied hydrogen peroxide on the web.

8. The apparatus as claimed in claim 2, wherein the injector injects heated air at a speed greater than a speed of the material web in the elongate chamber.

9. The apparatus as claimed in claim 2, further comprising means for heating the air for the injector before injection into the outer flow duct to a temperature sufficient to heat the flow mixture to 150° C.

10. An apparatus for sterilizing a continuous material web, comprising:
    a first treatment station including means for contacting an advancing material web with a liquid sterilizing agent; and
    a second treatment station including
        an inlet chamber having an inlet opening,
        an outlet chamber having an outlet opening,
        an elongated chamber connected to and extending between the inlet chamber and the outlet chamber,
        a return duct connecting the inlet chamber and the outlet chamber,
        means for injecting heated, sterilizing agent-free air into the return duct, and,
    means for guiding the material web through the second treatment station from the inlet opening in the inlet chamber, through the elongated chamber, and out the outlet opening in the outlet chamber, wherein the material web is simultaneously dried by heated air, so that the liquid sterilizing agent is vaporized to the gaseous state in an atmosphere of the second treatment station, and sterilized by gaseous sterilizing agent as the material web is advanced through the second treatment station,
    wherein the injecting means is directed to inject heated, sterilizing agent-free air to the return duct so that a flow circulates through the return duct, inlet chamber, elongated chamber, and outlet chamber to the return chamber, the heated, sterilizing agent-free air mixing with the flow and gaseous sterilizing agent returning to the return duct, and wherein the heated, sterilizing agent-free air circulates the mixture in the second treatment station in a direction of movement of the material web.

11. The apparatus as set forth in claim 10, wherein the contacting means includes a bath of liquid sterilizing agent through which the material web is drawn.

12. The apparatus as set forth in claim 10, wherein the contacting means includes sprayers for spraying sterilizing agent in liquid form on the material web.

13. The apparatus as set forth in claim 10, wherein the first treatment station includes a pair of nip rollers, the material web being drawn through a nip defined by the pair of nip rollers after the material web is contacted by the sterilizing agent in liquid form.

* * * * *